US00PP21382P2

(12) United States Plant Patent
Cully

(10) Patent No.: US PP21,382 P2
(45) Date of Patent: Oct. 12, 2010

(54) OAK TREE NAMED 'TABOR'

(50) Latin Name: ***Quercus robur*×*Quercus alba***
Varietal Denomination: Tabor

(76) Inventor: Earl Cully, 846 Hoagland Rd., Jacksonville, IL (US) 62650

( * ) Notice: Subject to any disclaimer, the term of this patent is extended or adjusted under 35 U.S.C. 154(b) by 11 days.

(21) Appl. No.: 12/316,911

(22) Filed: Dec. 18, 2008

(51) Int. Cl.
*A01H 5/00* (2006.01)

(52) U.S. Cl. ..... Plt./225

(58) Field of Classification Search ..... Plt./225
See application file for complete search history.

(56) References Cited

OTHER PUBLICATIONS

Dirr. Manual of Woody Landscape Plants 2009, 6th ed., pp. 937 and 939.*

USDA Natural Resources Conservation Service. Plants Profile *Quercus×bimundorum Palmer* [*alba×robur*] [online], [retrieved on Dec. 16, 2009]. Retrieved form the Internet <http://plants.usda.gov/java/profile?symbo1=QUBI2> 3 pages.*

* cited by examiner

*Primary Examiner*—June Hwu

(57) ABSTRACT

A new and distinct hybrid oak named 'Tabor' characterized by its broad-oval growth habit, dark, glossy green mildew resistant foliage, strong wood, orange-red fall color, and hybrid vigor.

8 Drawing Sheets

BACKGROUND OF THE INVENTION

The present invention comprises a new and distinct cultivar of a $F_1$ hybrid oak tree botanically known as *Quercus robur*× *Quercus alba* and referred to by the name 'Tabor'. The parent tree is growing in a cultivated area at the home of Earl Cully, 846 Hoagland Road, Jacksonville, Ill. 62650 in Morgan County, Township 14 north, Range 10 east. The 'Tabor' oak was selected from acorns collected at Carle Park in Urbana, Ill. The acorns were planted in the fall of 1975 and the 'Tabor' oak was selected from this cohort of seedlings.

BRIEF SUMMARY OF THE INVENTION

The 'Tabor' cultivar displays a broad-oval crown form, a straight central leader, and extremely glossy, dark green leaves. The parent tree is approximately 54 feet (16.5 meters) in height with a 48.5 foot (14.8 meters) spread after 32 years of growth. 'Tabor' shows hybrid vigor with growth having averaged 1.7 feet (52 cm) per year during this time. It has come through several ice storms and high wind events with no observed breakage of any branches indicating a very strong angle of branching and wood structure. 'Tabor' has proven winter hardy in the U.S.D.A. zone 5b in which it has been growing and has survived low temperatures of minus 28° F. (−33° C.) and unusual spring and fall freezes without any damage. With white oak (hardy in zone 3b to 9) as one of its parents, it would be reasonable to assume winter hardiness into zone 4b.

'Tabor' hybrid oak lends itself well to park, street tree, home lawn plantings where a large long lived tree would be desired. The unusual orange-red autumnal coloration distinguishes the 'Tabor' cultivar from other native oak species and cultivars in the eastern United States.

The pistillate parent of the 'Tabor' cultivar was determined to be English oak (*Quercus robur*) and the staminate parent has been determined to be white oak (*Quercus alba*). This unique heritage has resulted in some botanical traits that are characteristic of one or both parents while other traits are intermediate. The leaves are approximately the same size as white oak but an average leaf has 11 to 13 lobes which is more typical of English oak. The lobes of the 'Tabor' cultivar are longer and more obtuse than is typical for English oak which have short, rounded lobes. 'Tabor' oak has an intermediate peduncle length that varies from 1.8 to 4.3 cm while a typical white oak has a sessile to 1.3 cm long peduncle, and English oak has a peduncle length of 2.5 cm to 10.6 cm. The autumn coloration is an orange-red color which differs from English oak and white oak. English oak foliage typically has a yellow to brown fall color, and white oak foliage turns burgundy-red and then purple, but the intermediate orange-red autumnal color of 'Tabor' demonstrates its hybrid heritage.

Clones of the 'Tabor' demonstrate hybrid vigor and typically grow 5 to 6 feet in height after being grafted onto established two year-old swamp white oak (*Quercus bicolor*) rootstock with 90-95% success. This cultivar has been propagated by side-veneer and cleft grafting. Chip-budding has also been used to propagate this plant. Propagation has been performed at 846 Hoagland Road, Jacksonville, Ill. 62650 and in two different wholesale nurseries in Oregon.

DETAILED BOTANICAL DESCRIPTION

In the following description, color references are made to The Royal Horticultural Society Colour Chart.

BRIEF DESCRIPTION OF THE DRAWINGS

The accompanying colored photographs illustrate the appearance and color of the new 'Tabor' cultivar hybrid oak tree. These photographs show the color as is reasonably possible to obtain in colored reproductions of this type. Actual foliage colors may differ slightly due to light reflectance.

THE PLANT

Tree, Hybrid Oak

Figure 1:
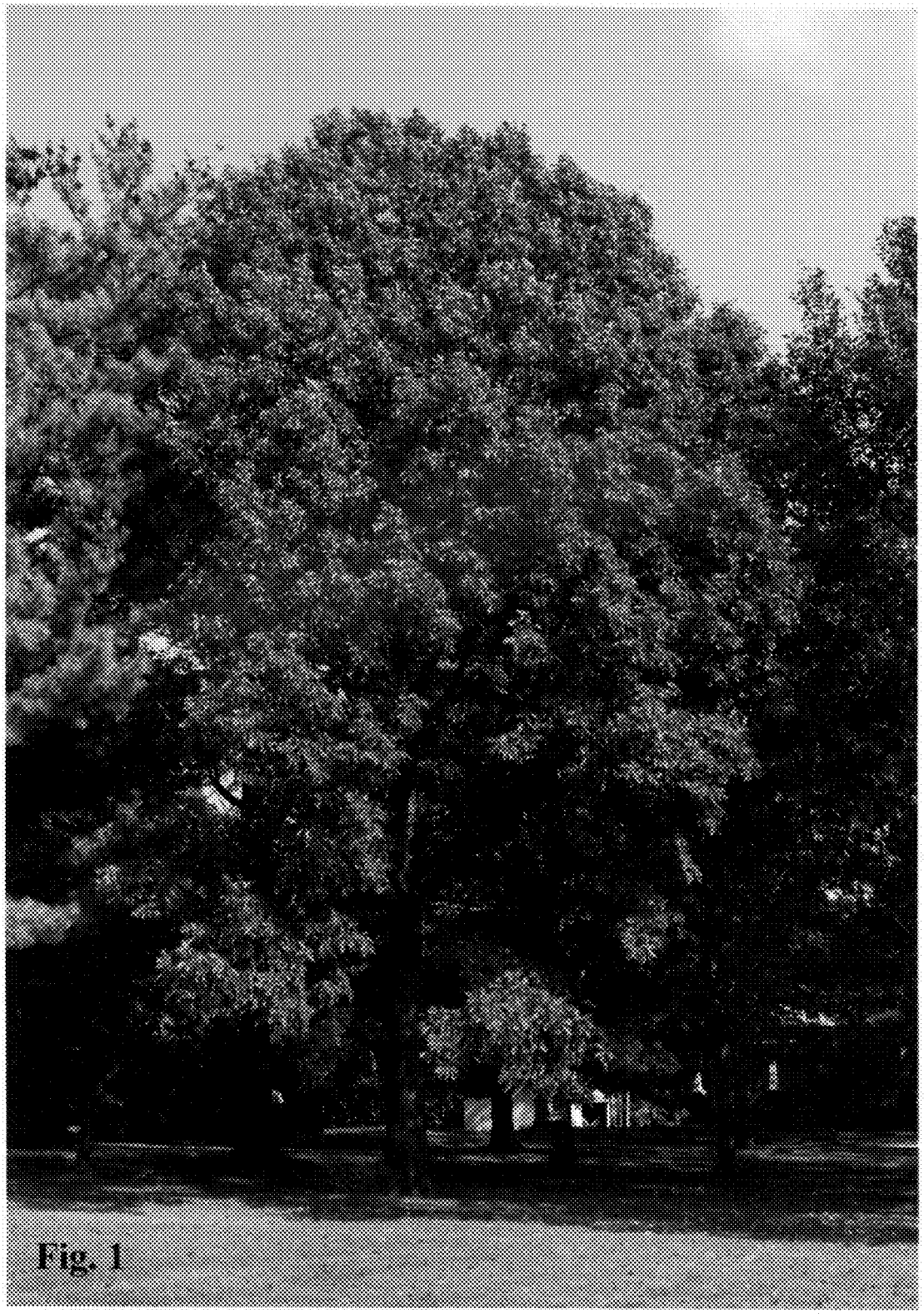
FIG. 1 depicts the initially discovered tree named 'Tabor' in summer foliage showing the broad, oval crown form and highly glossy, disease and powdery mildew free dark green foliage.
Figure 2:
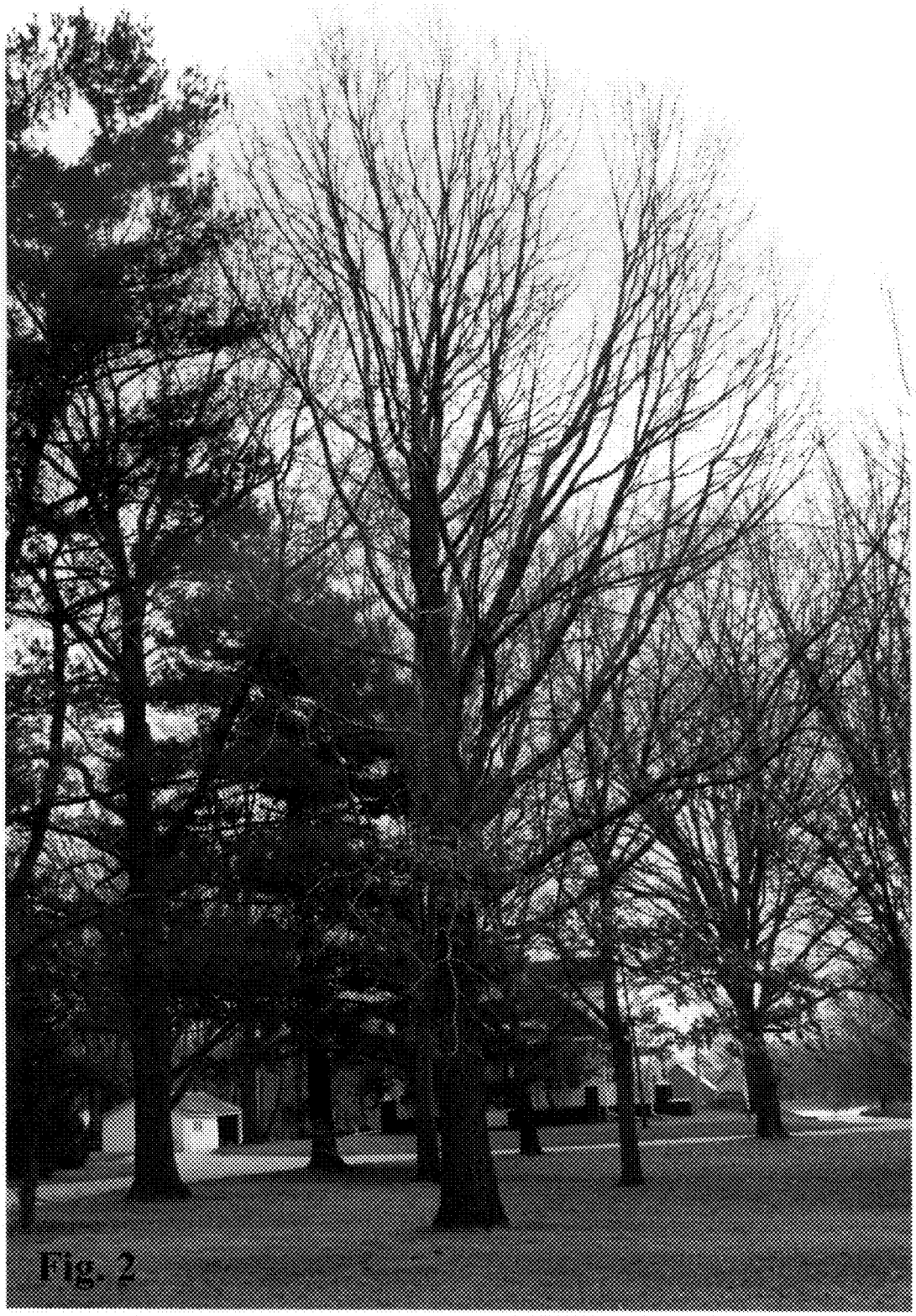
FIG. 2 depicts the 'Tabor' cultivar without foliage; thus, revealing its branching structure.
Figure 3:
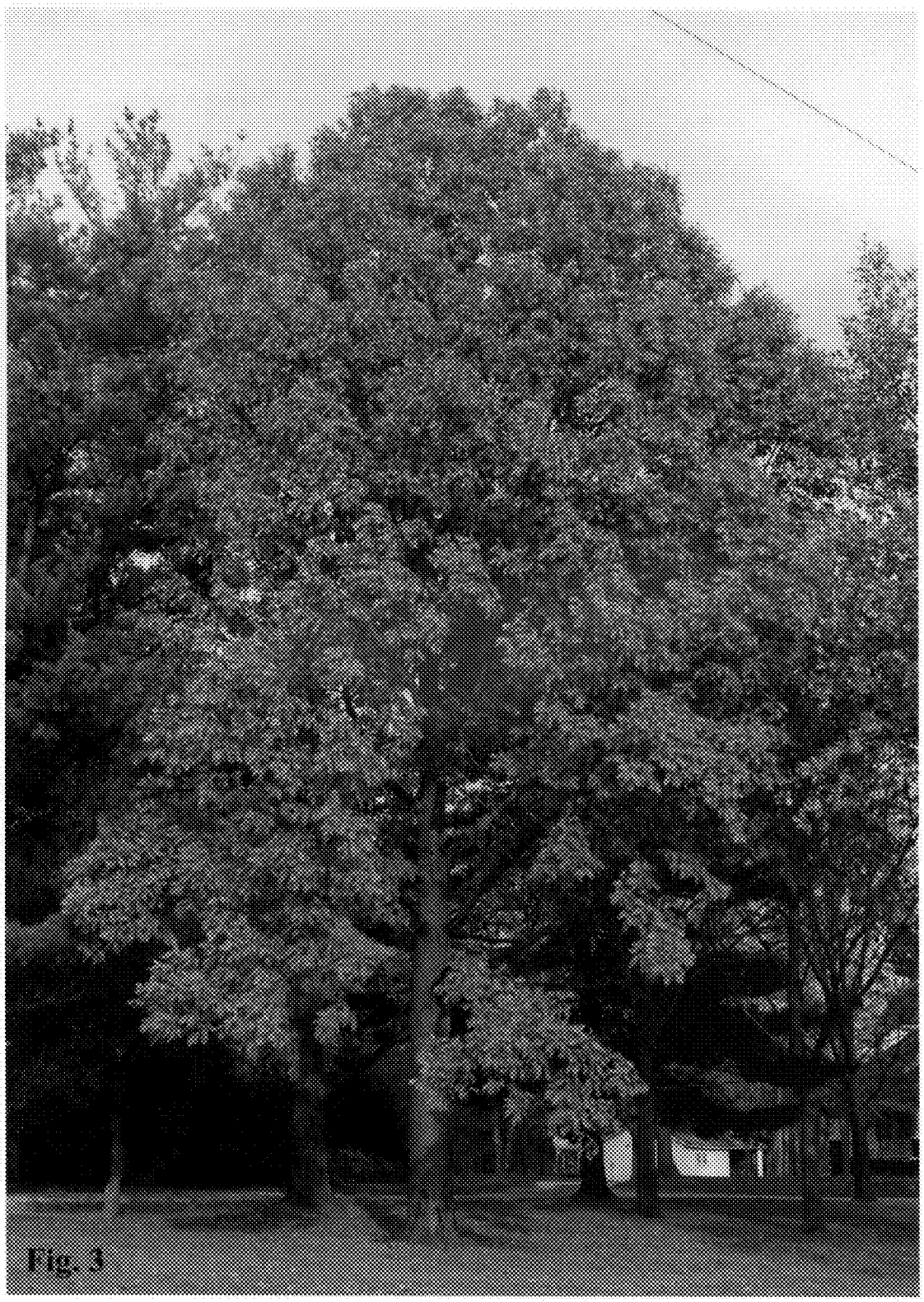
FIG. 3 depicts the Tabor cultivar in autumn showing the orange-red color.
Figure 4:
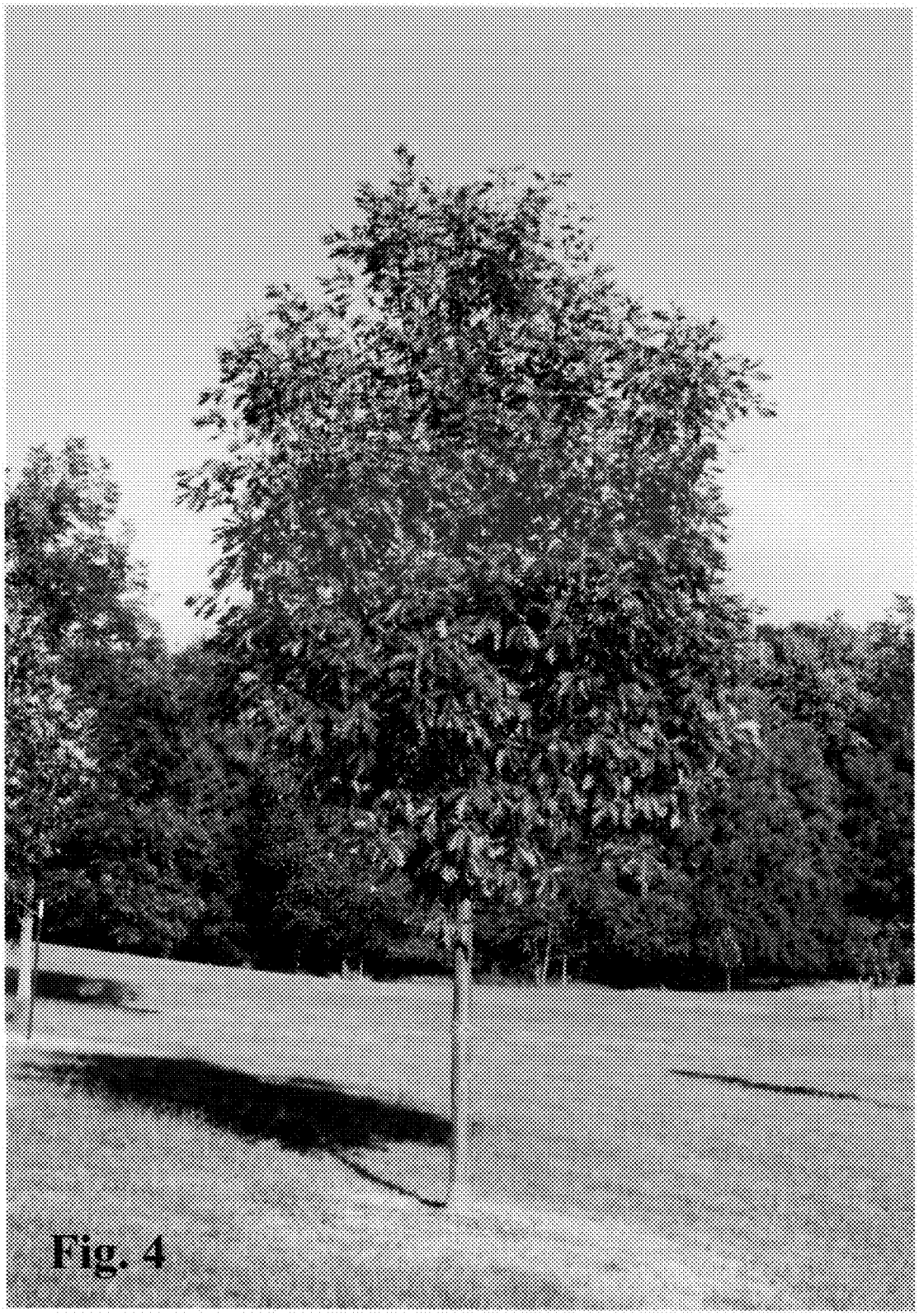
FIG. 4 depicts a clone of the 'Tabor' cultivar illustrating the same broad, oval crown form as the parent tree.
Figure 5:
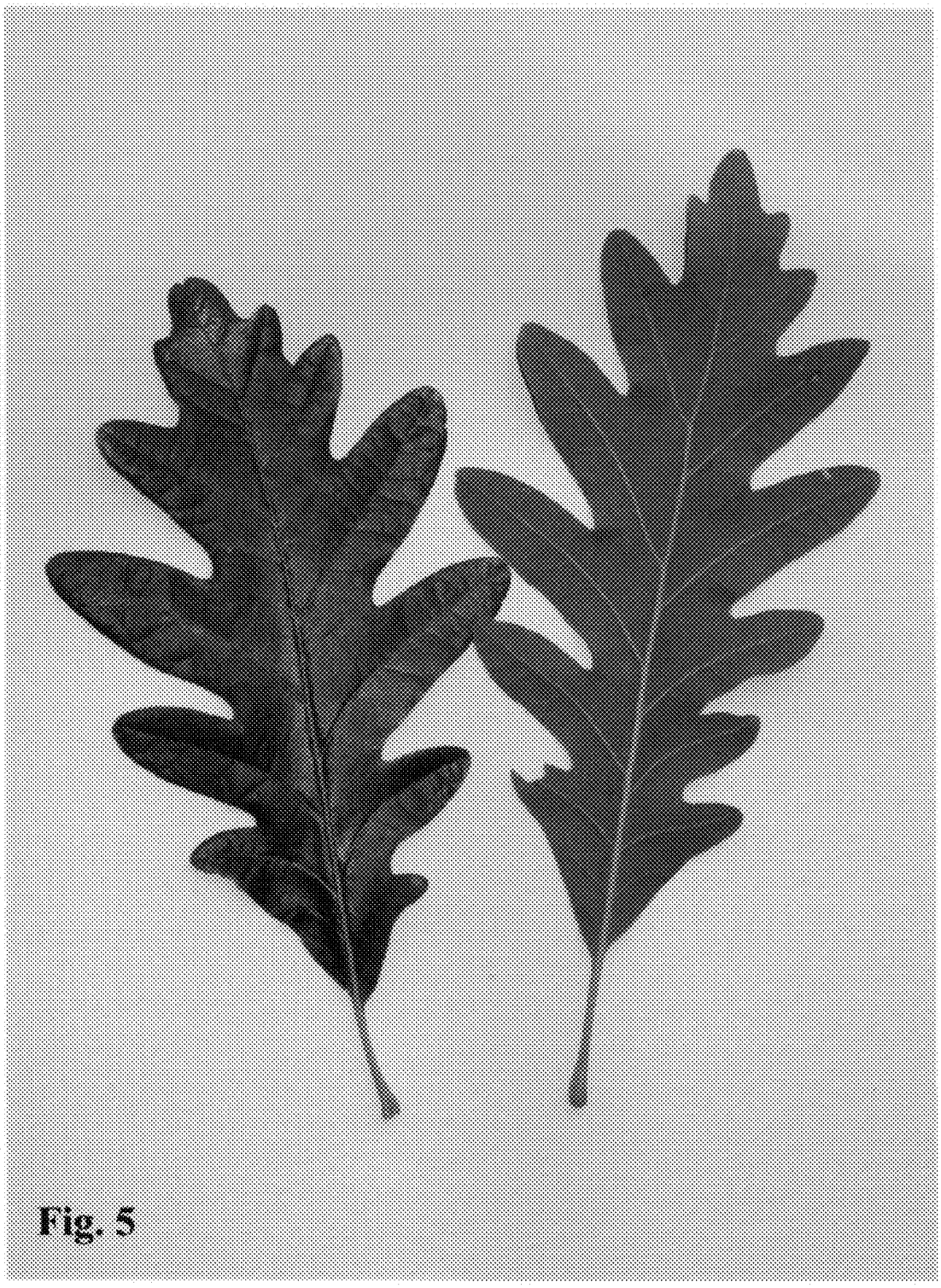
FIG. 5 depicts the powdery mildew resistant, dark green, glossy foliage of the 'Tabor' oak.
Figure 6:
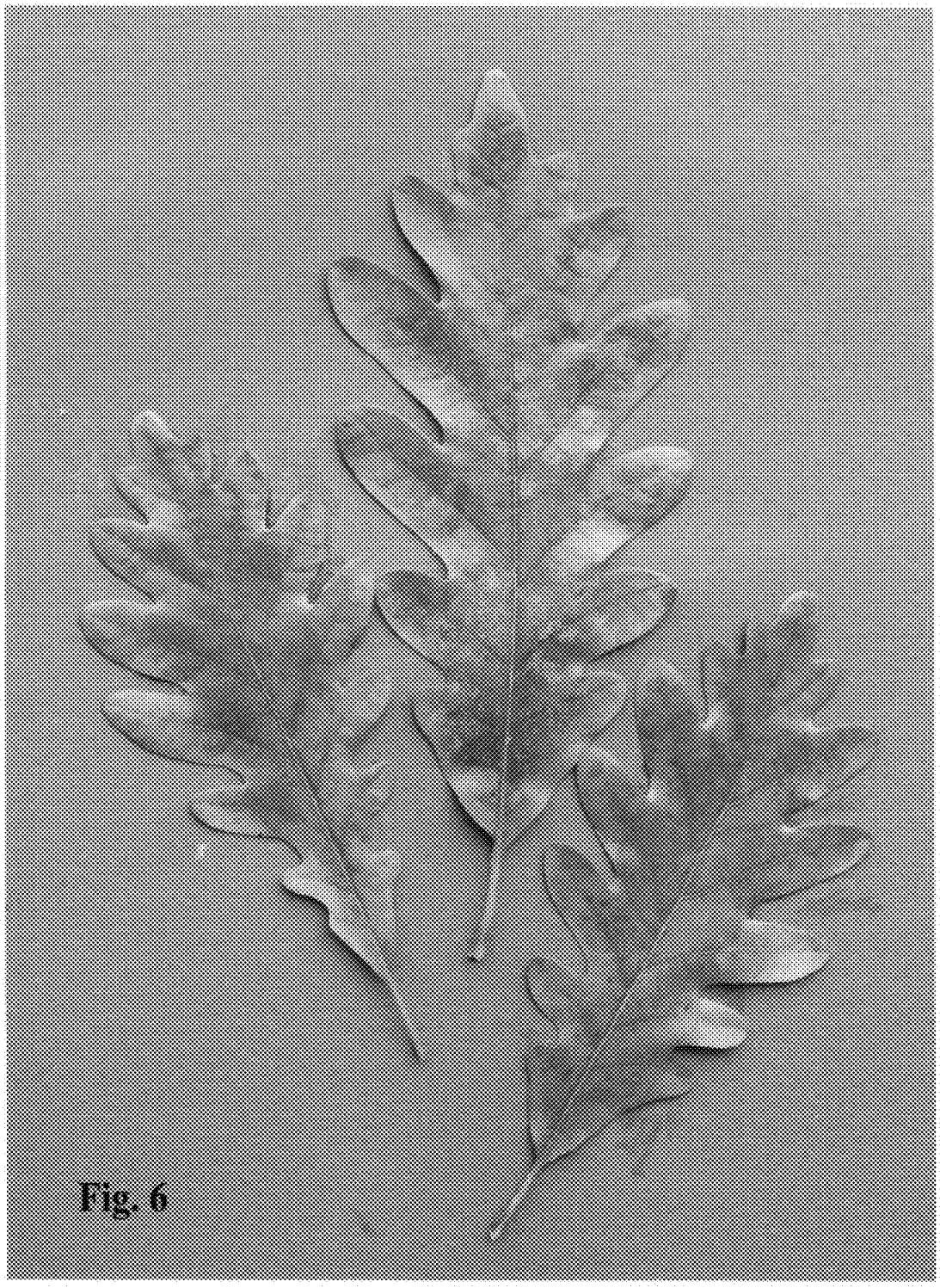
FIG. 6 depicts the autumnal leaf color (orange-red 32B and orange 26A).
Figure 7:
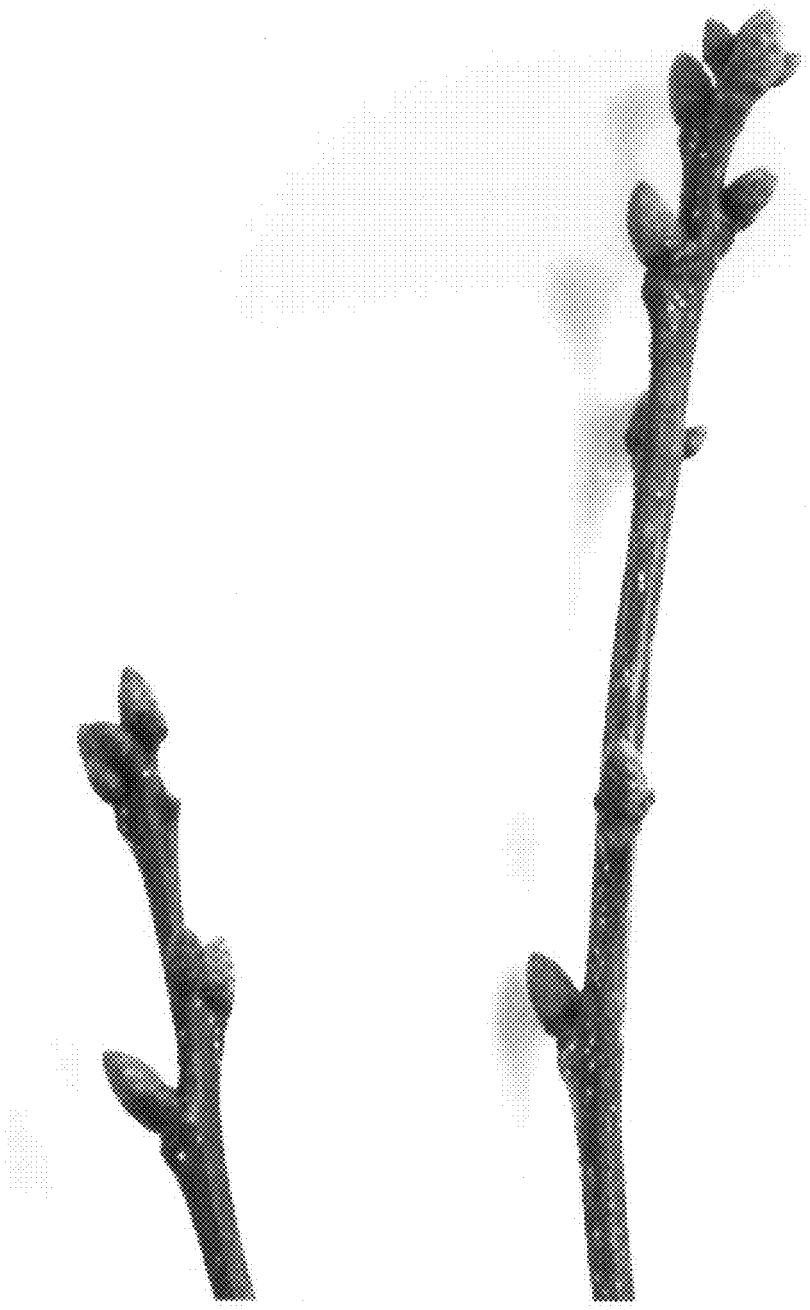
FIG. 7 depicts a twig, including terminal and lateral buds of the 'Tabor' oak.
Figure 8:
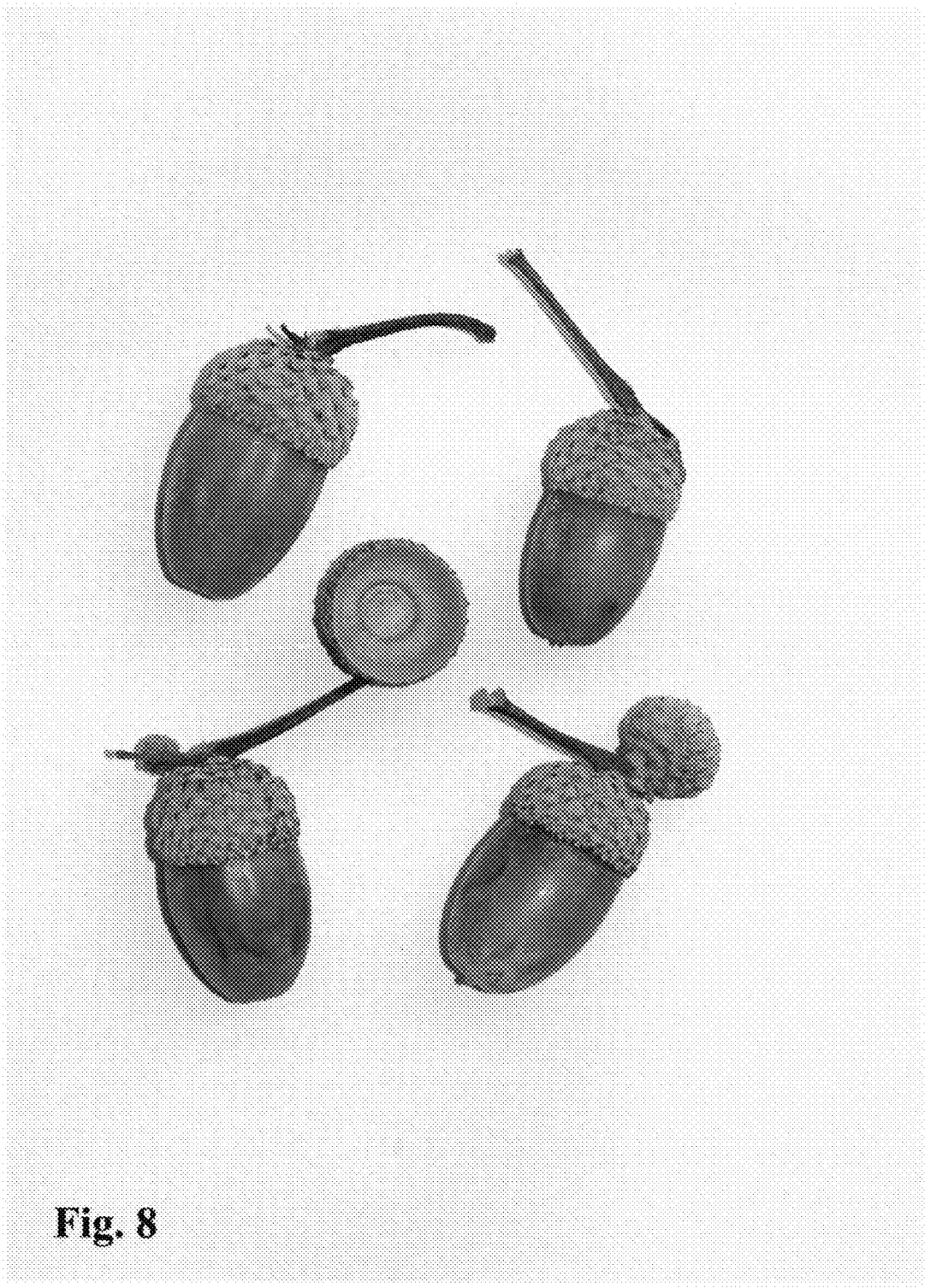
FIG. 8 depicts mature (brown) acorns of the 'Tabor' cultivar in early autumn.

Name: Cultivar 'Tabor'.

Parentage:

*Seedling or sport.*—Seedling.

*Seed parent.*—*Quercus robur.*

*Pollen parent.*—*Quercus alba.*

Classification: *Quercus robur*×*Quercus alba.*

Discovered: This seedling was selected from a row of seedlings in a cultivated area at the home of Earl Cully located at 846 Hoagland Road, Jacksonville, Ill. 62650, Morgan County, Township 14, Range 10. Presently, the tree is being propagated by chip budding or grafting onto two-year old swamp white oak (*Quercus bicolor*) seedlings at 846 Hoagland Road, Jacksonville, Ill. 62650 and at a two wholesale nurseries in Oregon.

Form: Tree.

Shape: Broad oval.

Height: 16.46 meters, 54 feet.

Spread: 14.78 meters, 48.5 feet.

Trunk size: Diameter at breast height (d.b.h) =58.6 cm, 23.1 inches (as measured at 1.37 meters, 54 inches above ground level).

Trunk base shape: Cylindrical.

Growth rate: Moderate to fast.

Strength: Excellent, no evidence of breakage.

Age:32.

Bark: furrowed vertically, breaking into long, blocky ridges.

*Alignment of pattern.*—Vertical furrows.

*Texture of bark.*—Moderately rough does not flake easily.

*Exfoliation.*—no exfoliation.

*Size of bark pattern.*—Plates (19.0-6.4 cm) average=9.3 cm long by (3.2-1.3 cm) average=2.2 cm wide.

Trunk bark color: Mostly grey 156A, with some grey-green 197A, and grey-green 198A.

Branches:

*Angle of attachment.*—Most branches varied between 60°-90°, with some upper branches at 30°.

*Spacing of branches.*—Moderately dense approximately 32 cm to 91cm between whorls of branches.

*Bark color.*—Grey (156B and C).

*Bark texture.*—Smooth on branches less than 5 cm diameter, with furrows developing on larger branch diameters.

*Bark exfoliation.*—No exfoliation observed.

*Small twig bark.*—(<0.7 cm diameter) (growing season) grey-green (195A,197A), grey-orange (177A), and grey (201A) (dormant season) grey-purple (183A), grey-green (197C), and grey (201A) Twig texture: Smooth overall but has small, warty lenticels.

*Lenticels.*—Small (0.05-0.1 cm), average=0.05 cm, round to oval orange-white (159B & C).

*Buds.*—Small triangular in shape (0.16 cm-0.79 cm), average=0.49 cm, scaled with a smooth texture and a fine pubescence on bud scales. The bud scales are arranged in an imbricate pattern with short grey-white (156D) hairs on the edge of the scales.

Leaves:

*Petiole.*—Length: (0.79-3.8 cm), average=2.3 cm. Color: Yellow-green (146D & C). Texture: smooth with no hairs and no warts present.

*Lamina.*—Length: (7.3 cm-24.6 cm), average=16.6 cm. Width: (4.45 cm-12.1 cm), average=7.0 cm. Form: Lamina obovate to oblanceolate. Shape of lamina base: Cuneate. Shape of lamina apex: Acute. Margin: Lobed. Texture: Membranous, glossy smooth upper surface. Quantity: Abundant. Color: Summer (upper) green (135A & B) (lower) green (136C) autumnal (upper) orange-red (32B), orange (26A) (lower) grey-orange (177D) grey-red (180D). Ribs and veins: 8 to 12 pairs of prominent veins yellow-green (150D); pinnate pattern of venation.

Flowers: Imperfect, monoecious; staminate aments are pendent, clustered with approximately 6 catkins per cluster, length 3.0-7.0 cm yellow-green (154B and 154 C); pistillate flowers are found in the axils of the emerging new leaves, ovary surrounded by a calyx 0.1-0.3 cm in length, color yellow-green (154A).

Fruit: Nut (acorn), acorn color of mature acorn is grey-orange (176A & 177A), length (cap and acorn) (4.0 cm-2.54 cm) average=3.4 cm, cap width (2.2 cm-1.9 cm) average=2.0 cm; length of the acorn (3.5 cm-2.1 cm) average=3.0 cm; cap length (1.4 cm-1.1 cm) average=1.3 cm; cap depth (1.3 cm-0.8 cm) average=1.0 cm; mature cap color is grey-brown (199B), immature cap color is a mixture of yellow-green (147C and 143C); peduncle length (4.3 cm-1.8 cm) average=2.7 cm; peduncle color grey-orange (166A); on average each peduncle held one developed acorn; imbricate scales on cap have a rough, warty texture; cap encloses 30% to 25% of the acorn.

Has this plant ever been offered for sale? No.

Compare this new variety with others of the same species and with its parents or parents; state the distinguishing characteristics of the new cultivar and its advantages.

This tree has a highly symmetrical broad-oval crown with extremely glossy, dark green leaves. The leaves posses an unusual shape exhibiting distinctive characteristics of the two different parent species *Quercus robur and Quercus alba*. The foliage of 'Tabor' most closely resembles white oak in size of the foliage and general outline of the leaf, but English oak shows its influence with a greater number of lobes per leaf than white oak and a longer acorn peduncle than white oak. The bark of 'Tabor' is also darker than white oak. The 'Tabor' hybrid oak has an orange-red autumnal coloration in contrast to red and burgundy fall color of white oak, or the yellow-brown fall color of English oak. The 'Tabor' hybrid oak differs from the Crimson Spire hybrid oak (*Quercus*×*bimundorum*) by having orange-red fall color instead of red and a broad oval crown form instead of columnar. 'Tabor' oak also differs from the 'Long' U.S. Plant Pat. No. 12,673 hybrid oak (*Quercus×warei*) and the 'Nadler' U.S. Plant Pat. No. 17,604 hybrid oak (*Quercusxwarei*) by having a broad crown form in contrast to the medium-oval crown from of 'Long' and the narrow columnar form of 'Nadler'. 'Tabor' hybrid oak shares the broad-oval crown form of the 'Clemons' U.S. Plant Pat. No. 11,431 hybrid oak. The orange-red fall color of 'Tabor' differs from the yellow-brown autumnal color of 'Clemons', 'Long', and 'Nadler' hybrid oaks.

It is claimed:

1. A new and distinct variety of hybrid oak tree *Quercus robur×Quercus alba* as illustrated and described herein.

* * * * *